US010424118B2

(12) United States Patent
Hannemann et al.

(10) Patent No.: US 10,424,118 B2
(45) Date of Patent: Sep. 24, 2019

(54) PERSPECTIVE REPRESENTATION OF A VIRTUAL SCENE COMPONENT

(71) Applicant: Siemens Healthcare GmbH, Erlangen (DE)

(72) Inventors: Thilo Hannemann, Erlangen (DE); Michael Suehling, Erlangen (DE); Michael Wels, Bamberg (DE); Andreas Wimmer, Forchheim (DE); Ferdinand Distler, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/390,827

(22) Filed: Dec. 27, 2016

(65) Prior Publication Data

US 2017/0200317 A1 Jul. 13, 2017

(30) Foreign Application Priority Data

Jan. 12, 2016 (DE) .................. 10 2016 200 225

(51) Int. Cl.
*G06T 19/00* (2011.01)
*G06T 7/13* (2017.01)
(Continued)

(52) U.S. Cl.
CPC .............. *G06T 19/006* (2013.01); *A61B 5/00* (2013.01); *A61B 6/032* (2013.01); *A61B 6/488* (2013.01);
(Continued)

(58) Field of Classification Search
None
See application file for complete search history.

(56) References Cited

U.S. PATENT DOCUMENTS

| | | | |
|---|---|---|---|
| 2005/0231530 A1* | 10/2005 | Liang ...................... | G06T 19/00 345/619 |
| 2010/0245352 A1* | 9/2010 | Chakraborty ........... | G06T 19/20 345/421 |

(Continued)

FOREIGN PATENT DOCUMENTS

| | | |
|---|---|---|
| DE | 102011075904 A1 | 11/2012 |
| DE | 102012201798 A1 | 8/2013 |
| WO | WO 2015006791 A1 | 1/2015 |

OTHER PUBLICATIONS

German Office Action Application No. 2015P00979 dated Oct. 11, 2016.

(Continued)

*Primary Examiner* — Frank S Chen
(74) *Attorney, Agent, or Firm* — Harness, Dickey & Pierce, P.L.C.

(57) ABSTRACT

A method and a device are disclosed for the perspective representation, via an output image, of at least one virtual scene component arranged within a real scene. In the method, depth image data of the real scene is captured from a first perspective via a depth image sensor, and 2D image data of the real scene is captured from a second perspective via a 2D camera. Further, a virtual three-dimensional scene model of the real scene is created with reference to depth information from the depth image data, and at least one virtual scene component is inserted into the three-dimensional virtual model. Finally, an output image is generated by way of perspective projection of the 2D image data corresponding to the second perspective onto the virtual three-dimensional scene model comprising the virtual scene component.

19 Claims, 3 Drawing Sheets

(51) Int. Cl.
*G06T 15/04* (2011.01)
*G06T 17/20* (2006.01)
*A61B 6/03* (2006.01)
*A61B 6/00* (2006.01)
*A61B 5/00* (2006.01)

(52) U.S. Cl.
CPC ............... *G06T 7/13* (2017.01); *G06T 15/04* (2013.01); *G06T 17/20* (2013.01); *A61B 6/5247* (2013.01); *G06T 2207/10028* (2013.01); *G06T 2207/10048* (2013.01); *G06T 2210/41* (2013.01)

(56) References Cited

U.S. PATENT DOCUMENTS

| | | | |
|---|---|---|---|
| 2012/0294504 | A1 | 11/2012 | Kyriakou |
| 2014/0142426 | A1 | 5/2014 | Razzaque |
| 2015/0022639 | A1 | 1/2015 | Blassnig et al. |
| 2015/0213646 | A1 | 7/2015 | Ma et al. |
| 2016/0163083 | A1* | 6/2016 | Barmpoutis ............ G06T 13/40 345/419 |
| 2016/0335809 | A1* | 11/2016 | Forutanpour ............. G06T 7/50 |
| 2017/0311896 | A1* | 11/2017 | Morger ................... A61B 5/70 |

OTHER PUBLICATIONS

Vivek, Rajan et al; "A realistic video avatar system for networked virtual environments"; Electronic visualization laboratory University of Illinois at Chicago; US; XP002770331; http://citeseerx.ist.psu.edu/viewdoc/summary?doi=10.1.1.18.6987&rank=1http://citeseerx.ist.psu.edu/viewdoc/download?doi=10.1.1.18.6987&rep=rep1&type=pdf; pp. 6; abschnitt 6; rendering the dead model; Abb. 3-5; 2002.

Sing, Vivek et al; "Estimating a patient surface model for optimizing the medical scanning workflow"; network and parallel computing; lecture notes in computer science; lect. notes computer; Springer international publishing; Cham, Bd. 8673 Chap. 59; Nr. 558; pp. 472-479; XP047312311; ISSN: 0302-9743; ISBN: 978-3-642-38492-9; pp. 472; letzter abs.; pp. 477; Zeile 1-3 Abb. 3; 2014.

Suma, Evan A. et al; "Rapid generation of personalized avatars"; IEEE Virtual rality (VR); IEEE; pp. 185; XP032479413; ISBN: 978-1-4673-4795-2; 2013.

Williams, N. et al; "Automatic image alignment for 3D environment modeling"; Computer graphics and image processing; Proceedings; 17th Brazil IAN Symposium on curitiba; pp. 388-395; XP010737848; DOI: 10.1109/SIBGRA.2004.1352985; ISBN: 978-0-7695-2227-2; 2004.

German Office Action and English translation thereof dated Oct. 7, 2016.

German Decision to Grant and English translation thereof dated Jul. 3, 2017.

* cited by examiner

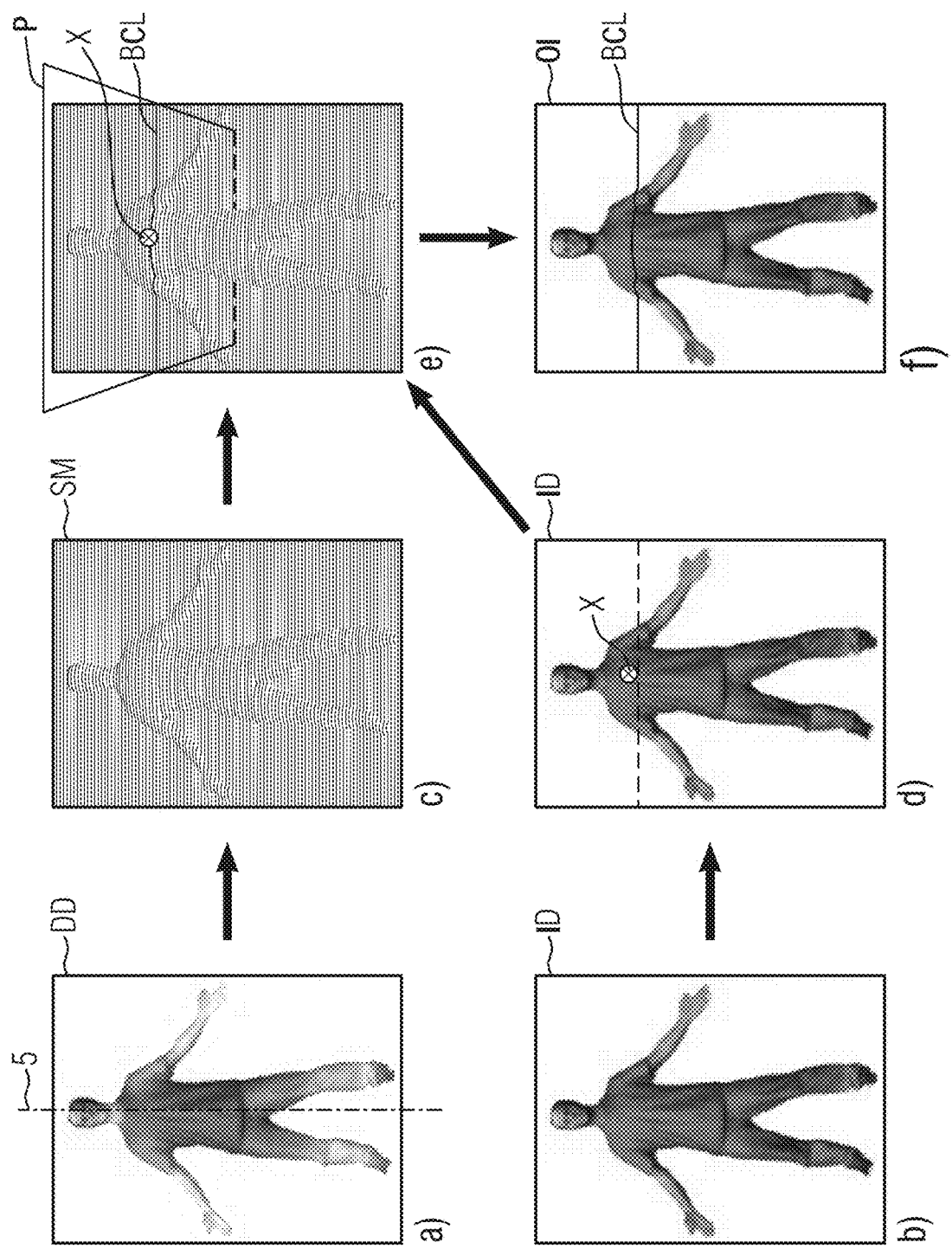

PERSPECTIVE REPRESENTATION OF A VIRTUAL SCENE COMPONENT

PRIORITY STATEMENT

The present application hereby claims priority under 35 U.S.C. § 119 to German patent application number DE 102016200225.2 filed Jan. 12, 2016, the entire contents of which are hereby incorporated herein by reference.

FIELD

At least one embodiment of the invention generally relates to a method and/or a device for the perspective representation of a virtual scene component, in particular a scan region boundary, which is arranged within a real scene, using depth information that corresponds to the real scene.

BACKGROUND

Before a measurement is performed using a medical imaging facility, it is usually necessary first to establish a so-called 'scan region', i.e. the region from which it is intended to record image data or acquire raw data during a 'scan routine' in order to generate the desired image data therefrom.

The scan region is often established with the aid of a topogram, which corresponds to a conventional X-ray projection from a single projection direction and maps the region of interest for the 'diagnostic' imaging (e.g. heart and lungs of an examination object). Start and end points for the actual image acquisition can then be superimposed on the topogram, e.g. manually. The start point and the end point of the scan region for capturing image data from a three-dimensional volume correspond to a spatial plane which is generally represented perpendicularly relative to the longitudinal axis of the examination object. The recording of a topogram nonetheless involves an additional dosage exposure, which per se conflicts with the ALARA principle generally prevalent in the field of radiology.

Without restricting the general applicability, an examination object is assumed in the following to be a patient, usually a human. However, the patient can also be an animal in principle. Therefore the two terms 'examination object' and 'patient' are also used synonymously in the following. However, the examination object can also be a plant or a non-living object, e.g. a historical artifact or similar.

Alternatively, a scan region can be defined by manually selecting a start line and an end line which are represented via a light aiming device via laser marking lines on an examination object, wherein said examination object lies on an object table (patient couch) which is part of the imaging facility and can be moved in a longitudinal direction (z-direction) relative to a scanner (e.g. the gantry of a CT facility). In this case, the longitudinal axis of the patient is usually parallel to the longitudinal direction of the object table, and the object table is usually situated outside the scanner. The start line and the end line extend in an essentially lateral direction (x-direction) of the object table, whereby the scan region is defined in a longitudinal direction of the patient. This setting via the light aiming device is however relatively time-intensive. In addition, the patient may consider the laser marking lines to be a nuisance.

It is also possible for a two-dimensional image of the examination object lying on the object table to be recorded using a camera and represented on a display at a control terminal or similar of the facility, wherein the start position and the end position of the scan region can be represented in the image by way of superimposed lines. However, the representation of a start point and an end point of the scan region by way of lines in the image is unfortunately not correct. The generation of the image in the camera can be compared to the pinhole camera model, according to which all optical rays intersect at one point, namely the pinhole diaphragm. Each pixel of the camera is assigned an optical ray containing those points in the space which could potentially be mapped onto this pixel. Each pixel in the image of the camera corresponds to the tonal value or color value of the object at the position where the optical ray passing through the pixel and the pinhole diaphragm intersects the object. The optical rays of all pixels therefore form a divergent beam of optical rays.

This does not correspond to the mapping geometry of the CT scan. The scan region is delimited by two parallel planes in the direction of movement (z-direction) of the object. The pixels corresponding to these planes in the image of the camera only form a straight line under very specific conditions, namely in the case of a telecentric mapping, i.e. a (virtually) infinite distance of the camera from the object in the pinhole camera model, or if the 'pinhole diaphragm' of the camera itself is located in the spatial plane that is to be indicated, i.e. directly above the start or end position. A telecentric mapping is structurally difficult to realize, since the entry lens system of the camera would need to be at least the size of the object. On the other hand, a camera which is situated in the spatial plane to be indicated can obviously be realized for only one selection of the spatial plane exactly, and is therefore unsuitable in principle for start position and end position simultaneously.

As a result of the geometry of the structure, in particular the fact that the camera requires a large angular aperture in order to fully capture the examination object from its position, e.g. on the ceiling of the room or on a gantry of a CT facility, the resulting error is not insignificant and precise setting of the scan region via an image captured using a 2D camera is not possible.

The error in the line representation caused by the pinhole camera model can be compensated, provided depth information is available for each mapped point of an object or scene. Depth information in this case is intended to comprise the distance of an object point, which is represented in a pixel, from the 2D camera. With reference to this depth information, it is possible to correct the course of the optical ray between object point and pinhole diaphragm and consequently to determine the actual pixel representing the object point concerned. By this means, it is possible to represent a scan region boundary in a 2D image with correct perspective.

However, this approach is inflexible and is limited to those components of a real scene which are actually mapped in the 2D image. Integration into the 2D image of other types of complex virtual scene components, which may be concealed by real scene components in the perspective of the 2D camera, e.g. a trajectory of an automatically mobile operating instrument in the context of intervention planning, or real components of the real scene which are likewise concealed, e.g. internal organs or elements which are concealed by the skin or surface of the examination object, was previously impossible or very complicated using known methods.

SUMMARY

At least one embodiment of the present invention provides an alternative method and/or device for the perspective representation of a virtual scene component arranged within a real scene, the method and/or device being particularly flexible in respect of deployment and consequently overcoming the disadvantages described above.

At least one embodiment is directed to a method and/or a device. Developments and advantageous embodiment variants are specified in the respective claims.

Inventive solutions to problems are described below, both with reference to embodiments of the method and with reference to embodiments of the device. Features, advantages or alternative embodiment variants cited in this context can also be transferred equally to the other embodiments of the subject matter and vice versa. In other words, inventive embodiments directed at a method, for example, can also be developed by features which are described in connection with a device. The corresponding functional features of the method are extended by corresponding inventive modules or units in this case.

At least one embodiment of the invention relates to a method for the perspective representation, by way of an output image, of at least one virtual scene component which is arranged within a real scene. The method comprises
  capturing depth image data of the real scene from a first perspective via a depth image sensor,
  capturing 2D image data of the real scene from a second perspective via a 2D camera,
  creating a virtual three-dimensional scene model of the real scene with reference to depth information from the depth image data, wherein a vircutal scene component is an object or element that is not contained in the real scene and thus is not imaged via depth image sensor and/or 2D camera,
  inserting at least one virtual scene component into the three-dimensional virtual scene model, and
  generating an output image by way of perspective projection of the 2D image data corresponding to the second perspective onto the virtual three-dimensional scene model comprising the virtual scene component.

An embodiment of the invention further relates to a device for the perspective representation, by way of an output image, of a virtual scene component which is arranged within a real scene, comprising
  a depth image sensor which captures depth image data of the real scene from a first perspective,
  a 2D camera which captures 2D image data of the real scene from a second perspective,
  a model-creation unit which creates a virtual three-dimensional scene model of the real scene with reference to depth information from the depth image data,
  an insertion unit which inserts a virtual scene component into the three-dimensional virtual scene model,
  a generation unit which generates an output image by way of perspective projection of the 2D image data corresponding to the second perspective onto the virtual three-dimensional scene model comprising the virtual scene component.

An embodiment of the invention also relates to a medical imaging facility, in particular a computer tomography apparatus, comprising a device according to an embodiment of the invention.

BRIEF DESCRIPTION OF THE DRAWINGS

The invention is explained again in greater detail below with reference to the appended figures and on the basis of example embodiments. Identical components in this case are denoted by identical reference signs in the various figures. The figures are not generally to scale.

FIGS. 3a-3f show an example embodiment of the inventive method with reference to captured image data of an examination object, scene model views of the examination object, and an output image which is produced according to the invention.

DETAILED DESCRIPTION OF THE EXAMPLE EMBODIMENTS

Figure 1:
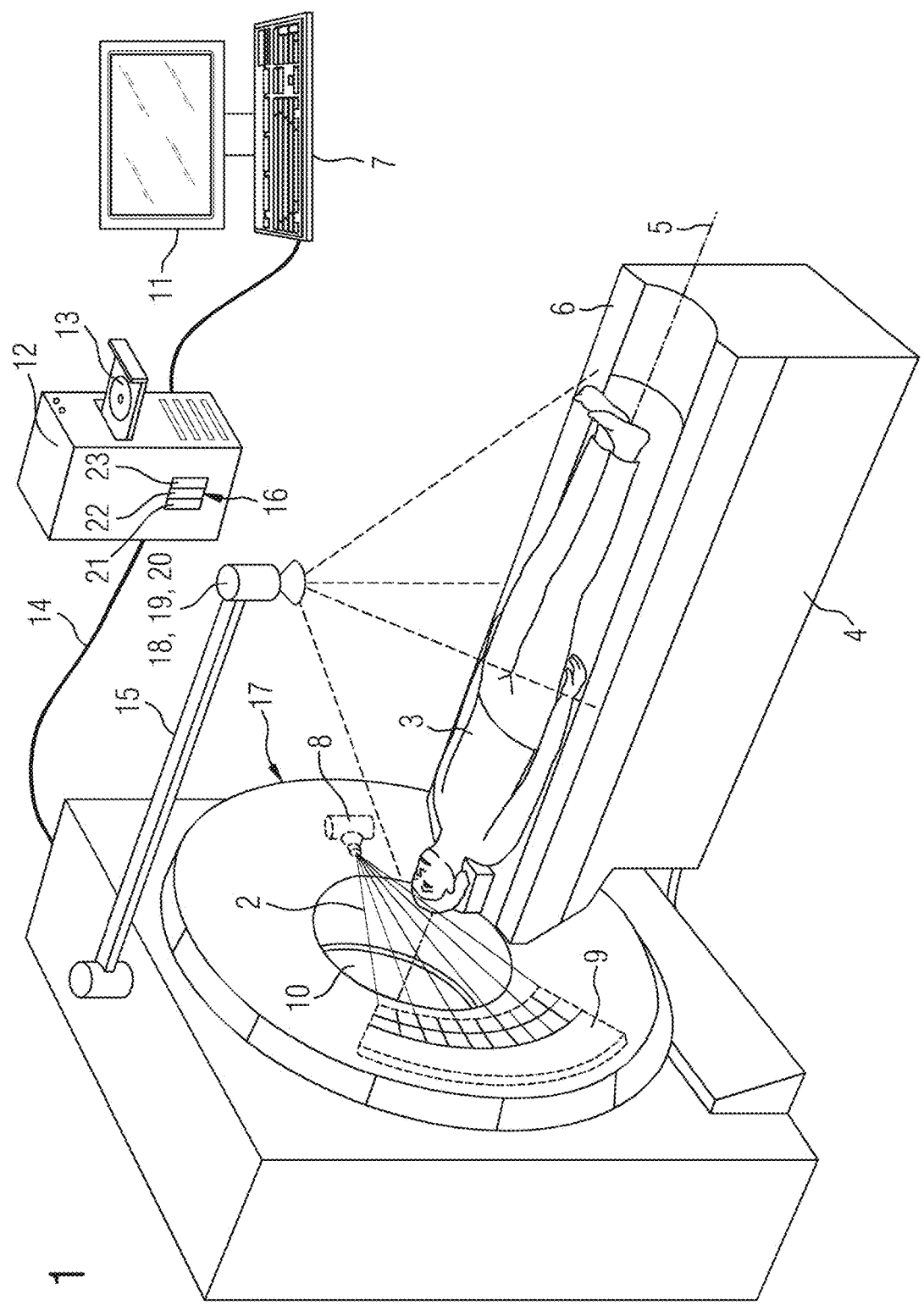
FIG. 1 shows a medical imaging facility in the form of a computer tomography device according to an example embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing"

or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes;

etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a method for the perspective representation, by way of an output image, of at least one virtual scene component which is arranged within a real scene. The method comprises
- capturing depth image data of the real scene from a first perspective via a depth image sensor,
- capturing 2D image data of the real scene from a second perspective via a 2D camera,
- creating a virtual three-dimensional scene model of the real scene with reference to depth information from the depth image data,
- inserting at least one virtual scene component into the three-dimensional virtual scene model, wherein a vircutal scene component is an object or element that is not contained in the real scene and thus is not imaged via depth image sensor and/or 2D camera, and
- generating an output image by way of perspective projection of the 2D image data corresponding to the second perspective onto the virtual three-dimensional scene model comprising the virtual scene component.

A method step of the method according to the invention captures of depth image data of the examination object from a first perspective. A further method step is the capture of 2D image data from a second perspective. The 2D image data comprises color values corresponding to the mapped object point for each pixel, e.g. using RGB data, wherein the attributes R-red, B-blue and G-green extend over a three-dimensional color space. In addition to the color values, the depth image data also comprises distance or depth information, D-distance, for the per-pixel mapped object point of the real scene relative to the camera, e.g. the depth image data is RGBD data. Other data formats and color spaces are possible. In particular, 2D and 3D data can be converted by way of known methods from one color metric to another, e.g. YUV, YCbCr or CMYK.

The inventors found that the depth image data can be used advantageously in a further step as a basis for generating a three-dimensional scene model of the mapped real scene. The scene model describes a virtual mathematical rendition of the real scene, describing the position, the course, the arrangement and/or orientation, etc. of the real scene components of the real scene relative to any system of coordinates and relative to each other.

In this case, a real scene is understood to be an arrangement relative to each other of any actually existing things, objects, etc. which are mapped. In particular, the real scene can correspond to an examination room in which an examination object is situated on a patient table of a medical imaging facility. As explained in greater detail below, this corresponds to the main application of the present invention.

According to an embodiment of the invention, it is now possible easily to insert any type and any number of virtual scene components, in particular three-dimensional virtual scene components, into this virtual scene. A virtual scene component can be any object or element which is not actually contained in the real scene and therefore not mapped by a depth image sensor and/or 2D camera. Its type, properties and information about its position, arrangement, orientation in said scene model, etc. can be established in advance by a user, for example, or automatically proposed as a function of a subsequently planned examination, possibly with reference to patient data, in particular information about the anatomy of said patient, and displayed to the user for confirmation or established without user input. It is thus possible from user inputs to determine e.g. a mathematical description of the virtual scene component, which can then be inserted into the virtual scene model while taking reference data relating to other scene components in the virtual scene model into consideration.

The output image comprising the perspective representation of the at least one virtual scene component is produced by perspectively projecting the 2D image data corresponding to the second perspective onto the virtual three-dimensional scene model comprising the virtual scene component. The three-dimensional virtual scene model including an inserted virtual scene component is therefore converted to the perspective of the 2D camera, such that the virtual scene component is correctly represented in the perspective of the 2D image data. In this way, the observer is advantageously provided with a representation of the real scene which corresponds to the image impression of the 2D camera image but includes the corresponding perspectively correct distortions which also act on the inserted virtual scene component.

An embodiment of the invention is therefore based on a departure from the conversion of a virtual scene component to a perspective of captured 2D image data on the basis of depth information, to instead propose the virtual modeling of the whole real scene, into which virtual scene components can easily be integrated in order then to represent the whole model including a virtual component from the 2D perspective.

This results in a position-planning representation which is correct, understandable and in particular familiar to the user due to the choice of perspective, and equivalent to a real scene. Additional exposure of the patient to radiation for the purpose of examination planning is not required, nor is any laborious forward and backward movement of the patient couch. The examination time can be minimized for the patient, since the duration of the patient in the imaging facility is minimized. The device becomes more economical with regard to manufacture, operation, service and repair, since components can be omitted entirely or used less intensively. This approach is moreover characterized by a particularly high degree of flexibility because 1) the approach according to an embodiment of the invention allows the real scene including an inserted virtual scene component to be observed from any chosen third perspective and 2) any number and any type of virtual scene components can be represented in correct perspective, i.e. allowing for any possible concealment of real scene components due to perspective.

According to a first embodiment variant of the invention, the perspective projection is provided by way of a renderer.

A renderer in this case is understood to be rendering software or a rendering pipeline which is used to generate a representation or visualization of three-dimensional bodies or objects. A volume renderer takes as a starting point a three-dimensional virtual model of the bodies or objects to be rendered. This is typically a virtual surface model or a virtual volume model. A surface model, e.g. in the form of a grid, describes interfaces or surfaces of the bodies or objects of the real scene that is to be mapped, whereas a volume model can also describe physical properties such as elasticity, density or similar of the mapped bodies or objects. The volume information can be described in particular by way of volume elements in the form of voxels. Values for individual volume elements are often provided in the form of so-called tonal values.

The voxel values are generally obtained via a medical imaging facility, for example. Measurements are typically made via computer tomography (CT), for example, and provide projections for various recording positions, from which the voxel values are reconstructed. Other possibilities include ultrasound methods or nuclear spin recordings (MRT). The voxel values are then usually provided in the form of so-called tonal values, which represent a measure for the respective density of the object at this location.

Using the voxel values, volume rendering generates a three-dimensional representation of an object or body on a two-dimensional display surface (e.g. a display screen of a medical imaging facility). So-called pixels are generated from the voxels in this case (possibly with the intermediate stage of deriving object points from the voxels via interpolation), and the image of the two-dimensional image display is composed of said pixels. In order to visualize three dimensions on a two-dimensional display, so-called alpha compositing and/or alpha decomposition is usually carried out. Using this standard method, voxels or volume points formed from voxels are assigned both colors and transparency values or more precisely opacity values (the term opacity is routinely used to express the transparency or the covering power of various layers of the body). Specifically, an object point is assigned e.g. three colors in the form of a 3-tuple which encodes the components of the colors red, green and blue (so-called RGB value) and a so-called alpha value which parameterizes the opacity. These variables together form a color value RGBA, which can be combined or mixed with the color values of other object points to give a color value for the pixel (for the visualization of partially transparent objects, usually via so-called alpha blending).

For the purpose of assigning a suitable color value, an illumination model is normally used. This illumination model allows for light effects (usually reflections of the light on surfaces of the object; these may be the outer surfaces or surfaces of inner layers of the object) during the modeled or simulated irradiation of the object for visualization purposes.

A range of illumination models are cited in the relevant literature. For example, the Phong model or Blinn-Phong model is widely used.

One of the most frequently used methods for volume rendering is so-called ray casting, or the simulation of light irradiation for the purpose of representing or visualizing the body.

In the case of ray casting, imaginary rays which start from the eye of an imaginary observer (this is also referred to as a virtual renderer camera) are transmitted through a body or an object. Along the rays, RGBA values for sampling points are determined from the voxels and combined to form pixels for a two-dimensional image via alpha compositing or alpha blending. In this case, illumination effects are usually taken into consideration via one of the aforementioned illumination models as part of a method known as 'shading'.

Accordingly, the 2D image data is inventively projected perspectively along the optical rays of the 2D camera onto the scene model. The second perspective of the 2D camera is therefore adopted for the virtual scene model. In other words, the virtual renderer camera is arranged in the same pose as the 2D camera, such that a realistic representation of the real scene including the at least one virtual scene component can be calculated and displayed from a viewing direction of the 2D camera.

This approach is based firstly on the finding that rendering software is very widely used, at least in the field of augmented reality, and in particular that individual rendering pipelines developed in-house, e.g. the Volume Rendering (VRT) feature of Siemens syngo, are available for the purpose of executing the inventive method and can be used to realize the invention at no cost. The invention consequently relies on existing technical solution frameworks. Secondly, the inventors have recognized that the existing algorithmic formulations from the field of augmented reality, used in conjunction with the depth information, can be transferred to the technical problem addressed by the invention of integrating virtual scene components into a 2D representation with correct perspective. Moreover, in addition to the change in observation direction, the use of rendering software also advantageously allows manipulation, e.g. coloring or clipping or similar, of image data which is contained in the virtual scene model and relates to the real scene that is represented. This means that the perspectively correct representation can have a higher information content depending on the application case.

According to a further embodiment variant, the perspective projection is effected with reference to extrinsic and/or intrinsic camera parameters of the 2D camera and/or of the depth image sensor. Both extrinsic and intrinsic camera parameters are produced when a camera is calibrated. As part of the intrinsic calibration, the internal geometry of the camera is determined, e.g. the focal length of the camera. It is also possible as part of the intrinsic calibration to determine correction functions for optical errors such as aberrations. It is also possible during the intrinsic calibration to make allowance for the centering of the sensor, misalignment of optical elements of the camera and/or other imaging errors. The intrinsic camera parameters obtained in this way can be used for the purpose of correcting the image data that has been captured.

As part of the extrinsic calibration, the pose of a camera in spatial coordinates is determined. Such spatial coordinates are also referred to as external coordinates or world coordinates. The pose is the combination of orientation and position. The pose can therefore be described by a rotation matrix and a position vector. In addition, the extrinsic calibration can also comprise positional differences between color sensor and depth sensor of the depth image sensor.

Both intrinsic and extrinsic calibration require a system of equations to be solved. Therefore known information must be provided in order to determine the unknown parameters of the system of equations. The unknown parameters are e.g. the focal length or an entry in the rotation matrix.

Whereas it is usually necessary to perform an intrinsic calibration for determining camera parameters only once, it is often necessary to perform an extrinsic calibration many times during the service life of a camera, e.g. whenever the pose of the camera changes.

Calibration methods which can be used in this context are known to a person skilled in the art and are therefore not explained in further detail.

In order to achieve a correct projection of 2D image data onto the virtual scene model, extrinsic camera parameters of the 2D camera and depth image sensor must be known. The calibration for this can either take place relative to a global system of coordinates, in particular a system of coordinates of a medical imaging facility, or directly between 2D camera and depth image sensor. The calibration can be performed for the purpose of determining the camera parameters in the context of the invention, or it can be assumed that the camera parameters are known.

A particularly simple embodiment variant of the invention is produced if the 2D image data and the depth image data are captured from the same or approximately the same perspective. In other words, first and second perspective do not differ or differ only imperceptibly. This has the advantage that the projection step of the method according to the invention can prove particularly simple, since it is now possible that only intrinsic camera parameters need be taken into account in this case. Furthermore, this approach allows 2D image data and depth image data to be recorded using just one camera, wherein the 2D image data then corresponds to e.g. the color data of the color sensor of the depth image sensor.

In an example embodiment of the invention, the 2D image data and the depth image data are captured simultaneously or quasi simultaneously (i.e. approximately simultaneously, with only a small time interval of a maximum of 1 s or less, for example). In this way, undesired movements within the real scene are not reflected in the image data and do not result in an incorrect relationship between 2D image data and depth image data.

According to a preferred embodiment variant of the inventive method, the virtual three-dimensional scene model is a surface model. This is characterized in that it is only produced when the depth image data is used. Accordingly, it represents all of the interfaces or surfaces of the objects, bodies, elements, etc. that are mapped in the real scene. In particular, this model does not contain any information about the nature, the internal structure and/or physical properties of objects in the real scene that is mapped. The model describes the interfaces or surfaces mathematically. In this case, the depth image data is preferably subjected to polygonization in order to obtain an optimal description of the mapped surfaces. Possible polygonization algorithms include e.g. triangulation, wherein surfaces are simulated via sequences of adjacent triangles. This method is therefore particularly suitable, because it is often also used by rendering software. Other model descriptions are also possible, e.g. a Cutting Cube algorithm. Alternatively, the surface can also be approximated using a model-based description via freeform surfaces. The use of only that information in the depth image data which relates to those surfaces that are mapped in the real scene is wholly sufficient for the main application case here, namely the perspectively correct representation of scan region delimiting lines, since in this case only the perspective of the 2D camera has to be simulated and in this sense 'included' via rendering software.

However, as mentioned above, embodiments of the invention are not restricted to scene models in the form of surface models. In particular, additional information relating to the nature, internal structure, etc. of objects in the real scene may be derived from other data sources and enhance the scene model. For example, existing image data about the examination object from previous examinations may be available from a medical imaging unit, in particular image data in the form of CT recordings, MRT recordings, etc. This image data either has a known geometric relationship to the scene model, or such a relationship can be established by way of a known registration method, such that the image information from the image data, in particular information about the nature, internal structure and/or physical properties, can be integrated into the scene model.

As mentioned above, according to a particularly preferred embodiment variant of the invention, the real scene comprises an examination object which is situated on a patient couch of a medical imaging facility, and the at least one virtual scene component corresponds to a scan region boundary of a scan region for which image data is to be captured via a medical imaging facility. This is understood to include the recording of a topogram, even though a topogram does not involve a 'scan' in the traditional sense. It is therefore also possible to delimit a topogram according to the invention. The scan region boundary can preferably take the form of a boundary contour line which runs along the surface of the mapped real scene in a curve of any profile. In particular, the boundary contour line runs transversely relative to a direction of movement of an object table on which the examination object is arranged or, in the case of topograms, in any plane which deviates from the plane that is perpendicular relative to the direction of movement of the examination object. However, the scan region boundary can also be configured in any desired position as a scan region delimiting plane.

Embodiments of the invention allow a scan region to be defined very precisely, since the course of a scan region boundary can simulated realistically on the basis of the scene model.

It is obviously possible to introduce more than one virtual scene component into the scene model. In an example of the invention, virtual scene components in the form of at least two boundary contour lines and/or boundary lines of a scan region can be introduced in the form of a start line and an end line between which the scan region is defined. Start line and end line are then represented at least within the lateral external outlines of the patient, though they can also extend beyond said outlines, in particular over the entire width of the 2D image. It is alternatively possible also to integrate other virtual scene components, e.g. one or more trajectories for intervention instruments or similar.

Embodiments of the inventive method prove to be particularly advantageous in this context since, in addition to an observation from the second perspective corresponding to the 2D image (main application case of the invention), the virtual scene model now also allows any desired further observation directions, such that the observer can gain an all-encompassing overall impression of the arrangement/position of the virtual scene component relative to the real scene. Moreover, the scene model can be enhanced by further image information in addition to the virtual scene component, such that e.g. internal organs of a patient or internal components of the real scene that are concealed in the 2D image, corresponding in each case to additional scene components from any desired source, e.g. from previous recordings made by a medical imaging facility, can easily be integrated into the model.

As mentioned above, in a further embodiment variant of the invention, the scan region boundary can correspond to a light marking or laser marking which is virtually projected onto the examination object. By this means, it is inventively possible to give the user of the imaging facility an image impression which is familiar from previous settings of the scan region. As a result of implementing the invention via a renderer, it is additionally possible to construct or realistically simulate any desired illumination effects or other types of visual effect.

By virtue of using rendering software, embodiments of the present invention also allow modifications (perspective change, coloring, clipping, etc.) to be made. In this case, a realistic representation is achieved by distinguishing between two essential effects. The first effect is the formation of shadows. This effect stems from the fact that, for a point on a simulated ray through an object, the path between the object point and the virtual light source or light sources includes obstacles, i.e. the light beam is not able to reach the object point unimpeded in some circumstances. In principle, the simplest method for calculating this shadow influence is to send a ray from the point concerned in the direction of the light source (or send rays to the various light sources), in order thus to determine which portions of the light are able to penetrate as far as the point.

Diffused light has a different effect (the term 'ambient occlusion' is often used in the specialist literature). This effect is attributable to diffused light and is therefore very important because it reveals structures which are not made visible by direct light alone. Generally, light diffusion first results in an object being struck by light from all directions. This diffused light can be absorbed by matter, thereby producing an uneven illumination of the object by the scattered light portion. A typical example of this effect is the corners of a room, which appear darker than its center. The absorption of diffused light is examined using e.g. the same method as used to determine the formation of shadows. However, since the diffused light does not come from one fixed source but from all directions, rays are sent stochastically from a hemisphere corresponding locally to a surface, whereby it is possible to check how much diffused light is absorbed. The sending of rays for the purpose of determining illumination properties is referred to as Ray Tracing, and stochastic ray sampling via 'ambient occlusion' is referred to as Monte Carlo Ray Tracing.

According to a further embodiment variant of the inventive method, the insertion of the virtual scene component into the virtual three-dimensional model is performed on the basis of user inputs. This allows the virtual scene component to be adapted in a particularly flexible manner according to the preferences of the user.

According to a further embodiment variant of the invention in this case, it can be particularly advantageous for the user to have the option of determining the arrangement of the virtual scene component using the 2D image data. This refers to the arrangement of the virtual scene component in the three-dimensional scene model. To this end, provision can be made for the 2D image data to be displayed to the user via e.g. a display device such as e.g. an LCD display, and for the user to be able to modify said data via an input device, e.g. a mouse with associated cursor or a touch-sensitive display. This advantageously corresponds largely to the procedure which is already known to the user.

According to another embodiment variant of the invention, the 2D image data of the examination object is captured in the visible wavelength range, i.e. between 380 nm and 780 nm, for example. The 2D image is preferably represented visually as a color image. Alternatively, representation as a grayscale image (with e.g. 256 shades) is likewise feasible. Recording of the 2D image data in the infrared range, e.g. between 780 nm and 1000 nm, is however also possible.

According to a preferred embodiment variant of the inventive method, the depth image data of the examination object is captured in the infrared wavelength range, e.g. between 780 nm and 1000 nm. This allows the depth image data to be determined in a particularly reliable manner. Other wavelength ranges for determining the depth image data are likewise possible.

An embodiment of the invention further relates to a device for the perspective representation, by way of an output image, of a virtual scene component which is arranged within a real scene, comprising
- a depth image sensor which captures depth image data of the real scene from a first perspective,
- a 2D camera which captures 2D image data of the real scene from a second perspective,
- a model-creation unit which creates a virtual three-dimensional scene model of the real scene with reference to depth information from the depth image data,
- an insertion unit which inserts a virtual scene component into the three-dimensional virtual scene model,
- a generation unit which generates an output image by way of perspective projection of the 2D image data corresponding to the second perspective onto the virtual three-dimensional scene model comprising the virtual scene component.

In particular, the depth image sensor can preferably be designed as a TOF camera ('time of flight' camera), e.g. comprising a photon mixing detector (PMD), which works via a propagation-time method with optically visible light or infrared light. Such units are relatively economical. Alternatively, the sensor can also provide the 3D data via a stereo-image method or via illumination using structured light or a combination thereof. The 2D camera can be a photographic camera or a video camera which produces 2D image data of the real scene.

The model-creation unit and/or the insertion unit and/or the generation unit can be designed and integrated in the form of e.g. software or software modules, e.g. in a control unit of a medical imaging facility, as explained in greater detail below. The individual units can be combined in a physical unit, or designed as separate units, in particular decentralized units. In any case, they have data connections to each other (wireless or wire-based) in order to be able to exchange the data that is required for the respective process steps. In particular, the insertion unit and/or the generation unit can be components of an existing rendering pipeline, which is typically realized as hardware.

In a preferred embodiment variant of the invention, the 2D camera and the depth image data sensor are combined to form a camera unit. This allows the recording of image data in 2D and 3D from the same or almost the same perspective. Camera unit in this case means that at least both cameras are arranged in a housing. Provision can be made for the optical axes of the 2D image camera and the depth image sensor to have a maximum deviation of approximately ±1% of a maximum dimension of the scan region. If the scan region has a length of 0.5 m in the z-direction, for example, the maximum deviation of the optical axes of the 2D image camera and the depth image sensor will be approximately 5 mm. The distance between the camera unit and an examination object or the geometric center thereof which is situated in the real scene is e.g. 2 m±50%, i.e. between 1 m and 3 m. In this way, it is possible to reduce the risk that the depth image data of the examination object contains erroneous data due to self-occlusion of the examination object. It is therefore possible to determine the scan region fully without interpolations or extrapolations of the depth image data which might have a corrupting effect. It is also easier thus to prevent an excessively low resolution and hence too few pixels, particularly in the depth image data. Alternatively, the 2D camera and the depth image data sensor can be combined not only spatially but also structurally and logically. In this type of configuration, the camera unit is designed in particular as a 3D camera in one of the variants described above, and is so configured as to generate 2D image data in addition to the depth image data, wherein the 2D image data can be produced as detector data from the color sensor, for example.

The camera unit can easily be mounted on a room ceiling or on a frame of a medical imaging facility, for example, and coupled (by wireless or wire-based means) to a control unit of said facility for signaling purposes.

FIG. 1 shows a medical imaging facility in the form of a computer tomography device. The computer tomograph shown here has a recording unit 17, comprising a radiation source 8 and a radiation detector 9. The recording unit 17 rotates about a system axis 5 during the recording of X-ray projections, and the X-ray source emits X-rays 2 during the recording.

A patient 3 lies on a patient couch 6 during the recording of X-ray projections. The patient couch 6 is connected to a couch base 4, such that this supports the patient couch 6 and the patient 3. The patient couch 6 is so configured as to move the patient 3 through the opening 10 of the recording unit 17 along a recording direction. The recording direction is usually described by the system axis 5, about which the recording unit 17 rotates during the recording of X-ray projections. In this example, the body axis of the patient is identical to the system axis 5. Both axes lie on the Z-axis of a three-dimensional Cartesian system of coordinates (not shown). In the case of a spiral recording, the patient couch 6 is moved continuously through the opening 10 while the recording unit 17 rotates about the patient 3 and records X-ray projections. The X-rays therefore describe a spiral on the surface of the patient 3.

The X-ray recording device has a camera unit 18. This comprises a 2D camera, which generates a two-dimensional representation of the mapped scene comprising the patient 3 in gray shades or color values, in a shared housing with a 3D camera or a depth image sensor, e.g. in the form of a stereo camera, time of flight camera or an interferometric system or similar, and comprises the necessary components for the respective recording technology, e.g. suitable light sources and detection units. In this example, the camera unit 18 is arranged above the patient couch 6 and is permanently connected to the image recording device via a retaining device 15. The camera unit 18 can also be attached to the rotatable recording unit 17. In particular, in the case of a rotatable recording unit 17 which can be tilted, the camera unit 18 naturally tilts at the same time. Alternatively, the camera unit 18 is arranged with an unrestricted view of the patient 3 in a stationary or mobile manner in the examination room, e.g. on the ceiling of the examination room, or arranged on a stand which can be moved freely in the examination room.

In this example embodiment, the real scene corresponds to the examination room with the patient 3 on the patient couch 6. Since both the 2D camera and the depth image sensor are combined in a camera unit, the first and the second perspective of the camera are identical or almost identical in this example embodiment.

In this example embodiment, the field of view of the camera unit 18 is large enough to capture the patient 3 fully in respect of length and width. Other embodiments of the field of view are also possible.

The computer tomograph has a computer 12 which is connected to a display unit 11, e.g. for the graphical display of X-ray image recordings or 2D image data of the 2D camera, and an input unit 7. The display unit 11 can be e.g. an LCD, plasma or OLED display screen. It can also be a touch-sensitive display screen which is also designed as an input unit 7. Such a touch-sensitive display screen can be integrated into the imaging apparatus or designed as part of a mobile apparatus. The input unit 7 is e.g. a keyboard, a mouse, a so-called 'touch screen' or also a microphone for voice input. The input unit 7 can also be so configured as to recognize movements of a user and translate these into corresponding instructions. An input unit 7 allows a user, for example, to transfer the position, arrangement, course, etc. of a virtual scene component in the displayed 2D image data, e.g. a boundary contour line for a scan region in this case, to the X-ray image recording device or to modify existing details relating to said scene component.

The computer 12 is connected to the rotatable recording unit 17 for the purpose of exchanging data. Via the connection 14, control signals for the X-ray image recording are transferred from the computer 12 to the recording unit 17 and projection data which has been recorded for the patient 3 can be transferred to the computer 12 for the purpose of image reconstruction. The connection 14 is either wire-based or wireless and is realized in a conventional manner. The computer 12 is also connected to the camera unit 18, in particular via the same connection 14, for the purpose of exchanging control signals or image data.

The computer 12 has an arithmetic unit 16. Said arithmetic unit 16 is designed as an image processing unit or image-data processing unit. In particular, it is configured to carry out all of the computational steps according to the inventive method in respect of the image data recorded by the camera unit 18. To this end, the arithmetic unit 16 comprises a model-creation unit 21 for creating or generating a three-dimensional virtual scene model from the depth image data of the depth image sensor 20, an insertion unit 22 which integrates the virtual scene component, e.g. as entered by the user, into the scene model at the correct position, and a generation unit 23 which generates an output image from the scene model comprising the virtual scene component by converting said scene model to the second perspective. To this end, the generation unit 23 refers to extrinsic and/or intrinsic camera parameters which allow for a position/pose difference of the two cameras and/or intrinsic mapping properties or mapping errors in each case. Provision is preferably made for said camera parameters to be retrievably stored in a memory (not shown) of the computer 12 or decentrally, or determined in the context of the method according to the invention. In particular, said insertion unit 22 and generation unit 23 are preferably part of an existing rendering pipeline.

The arithmetic unit 16 can interact with a computer-readable data medium 13, in particular in order to perform a method according to the invention via a computer program comprising program code. Furthermore, the computer program can be retrievably stored on the machine-readable medium. In particular, the machine-readable medium can be a CD, DVD, Blu-Ray disc, memory stick or fixed disc. The arithmetic unit 16 and therefore its subcomponents likewise can be developed in the form of hardware or software. For example, the arithmetic unit 16 can be designed as a so-called FPGA ('field programmable gate array') or comprise an arithmetic logic unit.

In the embodiment variant shown here, the memory of the computer 12 is used to store at least one computer program which performs all method steps of the inventive method when the computer program is executed on the computer 12. The computer program for executing the method steps of the inventive method comprises program code. Furthermore, the computer program can be designed as an executable file and/or stored on a computing system other than the computer 12. For example, the X-ray image recording device can be configured in such a way that the computer 12 loads the computer program for executing the inventive method into its internal working memory via an intranet or via the Internet.

Figure 2:
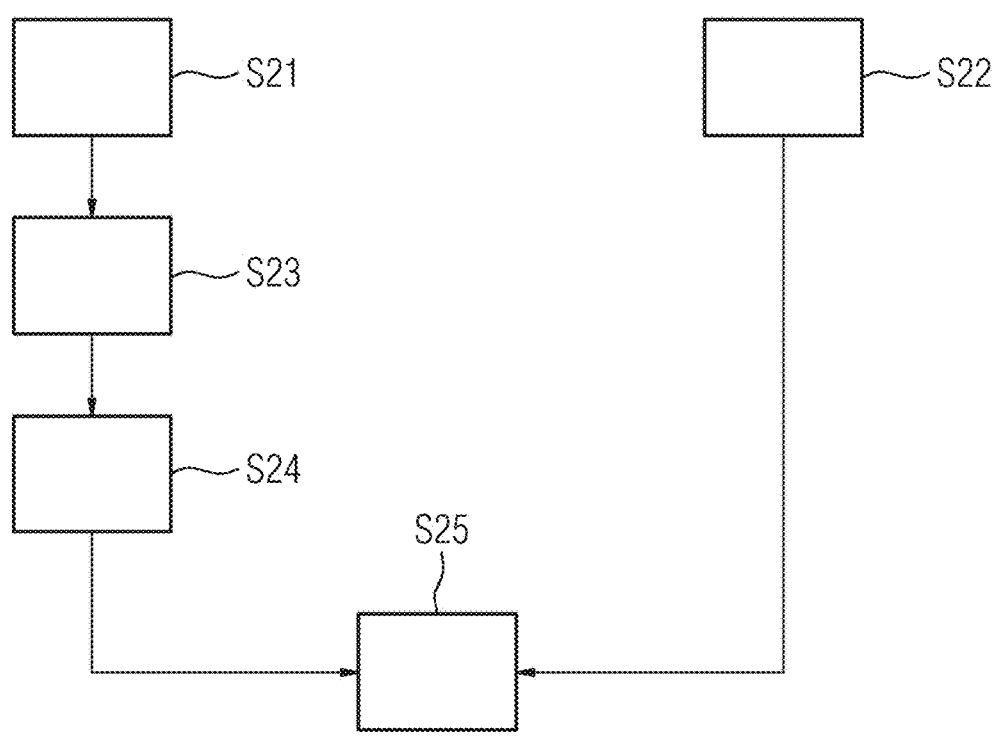
FIG. 2 shows a flow chart of the inventive method according to an example embodiment of the invention.

FIG. 2 describes an example embodiment of the method according to the invention. In a first step S21, depth image data DD of a real scene is captured from a first perspective. The capture in this case comprises both the recording of the depth image data DD comprising depth information via a depth image sensor 20 and, or solely, the transfer of depth image data DD to a postprocessing arithmetic unit 16. The real scene captured via depth image data DD maps a patient 3 who is lying on their back on a patient couch 6. The depth image data DD shows the patient 3 completely, but could also comprise image information relating to the patient couch 6 and possibly further scene components which are situated in the environment of the mapped patient and in the field of view of the depth image sensor, as represented schematically and in particular not to scale in FIG. 3a. Alternatively, the field of view of the depth image sensor may capture only one part or region of the body of the patient 3. For each image point or each pixel, the depth image data DD comprises depth information relating to the three-dimensional surface structure of the real scene, and describing a value for the distance of an object point from the depth image sensor 20. In the depth image data DD, a height is associated with a change in grayscale values. The grayscale values are high (dark) where e.g. the patient 3 has a significant height, e.g. as represented in the chest region, in the stomach region, at the arms or also in the face. The grayscale values are low (light) where the patient 3 has a modest height, e.g. in the neck region or at the legs at knee height. In particular, the surface of the patient 3 in terms of its shape or course is therefore captured in the first perspective. The depth image data DD is recorded in the infrared wavelength range (780-1000 nm).

In step S22, which takes place simultaneously or at least temporally close to step S21, 2D image data ID (FIG. 3b) is captured in the form of a photograph or video image. This capture comprises both the acquisition of the 2D image data ID via a 2D or 3D camera in a second perspective and, or solely, the transfer of the 2D image data to the postprocessing arithmetic unit 16. By virtue of the simultaneous or temporally close recording of depth image data DD and 2D image data ID, it is possible to avoid or reduce any variation of image information between the data records, e.g. due to movement of the patient 3. The 2D image data ID is captured in the optical wavelength range (380-780 nm).

First and second perspectives are identical in this case, since depth image sensor 20 and 2D camera 19 are realized by a single camera unit 18. The extrinsic camera parameters of both cameras 19, 20 are therefore the same. However, any desired and in particular differing poses and hence recording perspectives that are described exactly by the extrinsic camera parameters and can be interconverted via geometric transformations, e.g. translation or rotation, are conceivable for the two cameras.

In a further step S23, the model-creation unit 21 extracts the three-dimensional surface shape of the real scene comprising the patient 3 from the depth image data DD by converting the depth information into a virtual three-dimensional surface model SM. To this end, e.g. a point cloud representing the course of the surface is interpolated to give a smooth three-dimensional surface which is then described in model form, e.g. via sequences of adjacent triangles. Alternatively, the surface model SM describes the surface contour formed by the surface of the real scene viewed along the body axis of the patient 3, as illustrated in FIG. 3c by way of example.

It should be noted that the surface model SM can be completed in respect of regions of the scene surface which are missing due to e.g. superimposition, being omitted or not shown in the depth image data DD, in order to obtain a complete i.e. continuous three-dimensional surface model. This can be effected via known extrapolation methods or similar. In particular, this procedure then also allows observations of the real scene from perspectives other than the recording perspective of the camera unit 18, without necessarily resulting in image impressions which are troublesome to the observer due to missing image information. This however requires extrapolations of 2D image information relating to the surface of the real scene in some cases, in order that a meaningful image impression can be conveyed to the user.

Alternatively and/or additionally, the model-creation unit 21 can also create a volume model, using image data from other data sources for this purpose. In particular, it is possible to use e.g. X-ray image recordings of the patient 3 from previous examinations, representing e.g. internal organs of a relevant region in terms of their position, shape, size and/or physical properties or similar. If necessary, a spatial relationship between depth image data and X-ray image recordings can be established via known registration methods, thereby allowing the additional image information to be correctly positioned within the scene model.

However, such extensions of the scene model are omitted in the present example embodiment.

In a step S24, at least one virtual scene component VSC is inserted into the three-dimensional scene model SM. For this purpose, it is first necessary to have or create a geometric description of the virtual scene component VSC. In this example embodiment, it is intended to insert a scan region boundary, in particular a start line for a scan region. In this case, the start line lies in a start plane, which runs vertically and perpendicularly relative to the longitudinal patient axis 5 in this example embodiment. A start plane has been typically represented as a straight line in the 2D image data ID (dashed line in FIG. 3d). This serves merely as an example illustration and need not correspond to an actual start plane. However, the course of this line does not take the perspective distortions or mapping errors of the 2D image data ID into consideration, and therefore the course of the straight line will not generally represent the exact course of the curve of intersection between start plane and surface of the mapped real scene. In order to overcome these inaccuracies, provision can be made for the 2D image data ID which is normally used for planning the examination to be presented to the user via the display unit 11, and for the user to mark via input unit 7, in particular a touch screen, a position on the surface of the patient which should lie within the start plane. Provision can also be made for the user to be guided by anatomical landmarks or additional reference markings in the real scene, which help the user when marking the position. Alternatively, provision can be made for the computer 12 to propose a position as a function of the desired examination and/or the body region of interest, and for the user to confirm or reject the proposed position. In the present case, a position X which should lie within the start plane is marked by way of example in the chest region of the patient 3 (FIG. 3*d*). Still in step S24, it is now possible to determine the plane P (FIG. 3*e*) which runs vertically and perpendicularly relative to the longitudinal patient axis 5, and which includes the marked position X. At the same time, extrinsic and/or intrinsic camera parameters can be used in the general application case to produce the correct spatial relationship between 2D image data ID and depth image data DD or scene model SM. The plane defined by the position X cuts the surface of the patient 3 or real scene corresponding to scene model SM along a profiled curve, a so-called boundary contour line BCL. The course of this boundary contour line BCL is determined on the basis of the scene model SM and inserted into the scene model SM (FIG. 3*e*).

In step S25, the generation unit 23 determines an output image CI (FIG. 3*f*) from the scene model SM comprising the virtual scene component VSC for the perspective of the 2D camera 19, by projecting the 2D image data ID along the optical rays of the 2D camera 19 onto the scene model SM. This produces a representation of the boundary contour line BCL which is realistic, familiar to the user and in particular perspectively correct. Intrinsic camera parameters may be used in this context to compensate mapping errors of the 2D camera 19 and/or the depth image sensor 20.

The output image CI cannot be distinguished from the 2D image data ID according to FIG. 3*b* in terms of the image information that is represented perspectively, and therefore corresponds to a representation which is equivalent to a real scene. Unlike the 2D image data, however, the output image CI also includes a perspectively correct representation of the boundary contour line BCL. This is characterized in that its course differs at least in the region of the patient body from the course of the conventional marking line (dashed line) for the start plane. To be precise, relative to the dashed line it is shifted in the direction of the head of the patient 3 according to the height information from the depth image data DD. In the region of the couch 6 and the external outline of the patient 3, the dashed line and the boundary contour line BCL coincide in each case because the heights are zero there. It is assumed for the sake of simplicity in this case that the height of couch 6 is defined as a base 'zero' in a height direction. For this reason, the couch 6 in the depth image data DD is also uniformly white, since all regions of the couch 6 are situated at approximately the same height level.

Accordingly, regions of the patient body which were previously incorrectly excluded now belong to the scan region. The dashed line is only included in FIG. 3*f* in order to better illustrate the differences relative to the boundary contour line BCL, but is not contained in the output image itself.

It is of course possible to adopt any other desired camera position, in particular positions which differ for 2D camera and depth image sensor, from which the real scene comprising the virtual scene component VSC can be observed in correct perspective.

Further virtual scene components and/or virtual scene components other than a scan region boundary for a scan region can also be inserted according to the procedure described above.

It should be noted that both the method described in detail above and the illustrated device are merely example embodiments, which can be modified in all manner of ways by a person skilled in the art without thereby departing from the scope of the invention. In particular, individual steps of the inventive method of an example embodiment may be picked out and combined with method steps of other example embodiments insofar as this is technically possible and suitable. Although the invention is described for use with a computer tomography facility, for example, this does not exclude its advantageous use with other medical imaging facilities, for example:

- other X-ray facilities, e.g. for creating conventional X-ray scans or fluoroscopic inspections;
- magnetic resonance tomography devices (MRT);
- scintigraphs, positron emission tomographs (PET), single-photon-emission computer tomographs (SPECT);
- sonographs or color Doppler devices;
- diagnostic thermographs;
- electric impedance tomographs (EIT); or
- endoscopes.

Embodiments of the present invention is briefly summarized again below. According to an embodiment of the invention, virtual modeling is used for all scene components, real and virtual. Furthermore, in order to allow the flexible representation of virtual scene components, the invention makes use of known rendering pipelines, in particular rendering pipelines which have been developed in-house. For this purpose, a real scene into which a virtual scene component must be integrated is first converted from previously captured 3D depth information relating to the real scene into a three-dimensional model, i.e. virtualized.

As well as capturing 3D depth information, provision is also made for capturing 2D image data of the real scene, either from the same or a different perspective. Using extrinsic and/or intrinsic camera parameters from the calibration of the 2D camera and the 3D camera, the 2D image data is projected along the optical rays onto the virtual three-dimensional model of the real scene. If the same camera parameters are applied to a so-called virtual 'renderer camera', the virtualized real scene is represented in an uncorrupted i.e. perspectively correct manner, and can be enhanced by virtual scene components in the sense of an 'augmented reality'. Without additional virtual scene components, the pixels of an output image are reproduced exactly according to the 2D image data from the perspective of the 2D camera.

The freedom to add any desired virtual scene components to this representation allows the additional mapping of complex effects such as illumination via laser marker. It is possible when virtualizing the real scene, e.g. for any pixel of an RGBD image (depth image data), for a rectangle that is directed at the focal point of a 2D camera and scaled accordingly to be modeled as a virtual scene component at a distance from the 2D camera which is derived from the depth image data. The rectangles can be tilted according to the local gradients of the depth information in order that the directed portion of the reflection is correctly modeled subsequently, or interconnected to form a continuous surface network. A renderer or graphics pipeline then creates a view of the scene from any desired perspective. If the virtual camera is brought into line with the 2D camera, taking known camera parameters into consideration (e.g. field of view, image distortion, etc.), the 2D image data is represented in uncorrupted form, since the rectangles are represented seamlessly alongside each other from the original perspective. Any chosen further virtual scene components are represented correctly by the renderer, i.e. in respect of occlusions, etc., relative to the real modeled scene components. As a result of allowing for the perspective distortion of the 2D camera, the image impression that is thereby achieved in respect of the output image cannot be distinguished from the 2D image data.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for perspective representation, via an output image, of at least one virtual scene component arranged within a real scene that includes an examination object, the method comprising:
   capturing depth image data of the real scene including the examination object from a first perspective via a depth image sensor;
   capturing 2D image data of the real scene including the examination object from a second perspective via a single 2D camera;
   creating a virtual three-dimensional (3D) surface model of the real scene by converting depth information from the depth image data into the virtual 3D surface model such that the virtual 3D surface model describes a contour of a surface of the examination object, the depth information indicating a depth of the examination object;
   inserting the at least one virtual scene component into the virtual 3D surface model at a location corresponding to a desired start point for medical imaging the examination object, the at least one virtual scene component being an object or element that is not contained in the real scene and is therefore not imaged via at least one of the depth image sensor and the single 2D camera, the inserting including (i) creating a geometric description of the at least one virtual scene component, the geometric description including a profile curve representing the depth of the examination object, and (ii) inserting the at least one virtual scene component into the virtual 3D surface model based on the profile curve such that a curvature of the at least one virtual scene component in the virtual 3D surface model corresponds to the depth of the examination object;
   generating the output image using perspective projection to project the 2D image data corresponding to the second perspective along optical rays of the single 2D camera onto the virtual 3D surface model including the at least one virtual scene component such that the output image is a 2D image illustrating a perspectival correct version of the at least one virtual scene component; and
   setting a scan region for the medical imaging of the examination object based on the perspectival correct version of the at least one virtual scene component included in the output image.

2. The method of claim 1, wherein the perspective projection is effected via a renderer.

3. The method of claim 2, wherein the perspective projection is effected with reference to at least one of extrinsic and intrinsic camera parameters of at least one of the single 2D camera and the depth image sensor.

4. The method of claim 3, wherein the 2D image data and the depth image data are captured from a same perspective.

5. The method of claim 1, wherein the perspective projection is effected with reference to at least one of extrinsic and intrinsic camera parameters of at least one of the single 2D camera and the depth image sensor.

6. The method of claim 5, wherein the 2D image data and the depth image data are captured from a same perspective.

7. The method of claim 1, wherein the real scene includes the examination object, situated on a patient couch of a medical imaging facility, and
   the at least one virtual scene component corresponds to a scan region boundary.

8. The method of claim 7, wherein the scan region boundary corresponds to a light marking or laser marking which is virtually projected onto the examination object.

9. The method of claim 7, wherein the at least one virtual scene component corresponds to a boundary contour line as the scan region boundary.

10. The method of claim 1, wherein the inserting of the at least one virtual scene component into the virtual 3D surface model is effected based on user inputs.

11. The method of claim 10, wherein an arrangement of the at least one virtual scene component is determined using the 2D image data.

12. The method of claim 1, wherein the 2D image data of the real scene is captured in an optical/visible wavelength range.

13. The method of claim 1, wherein the depth image data of the real scene is captured in an infrared wavelength range.

14. A device for perspective representation, via an output image, of at least one virtual scene component arranged within a real scene that includes an examination object, the device comprising:
   a depth image sensor, to capture depth image data of the real scene including the examination object from a first perspective;
   a 2D camera to capture 2D image data of the real scene including the examination object from a second perspective; and a memory and a processor, the memory containing computer readable code that, when executed by the processor, configures the processor to, create a virtual three-dimensional (3D) surface model of the real scene by converting depth information from the depth image data into the virtual 3D surface model such that the virtual 3D surface model describes a contour of a surface of the examination object, the depth information indicating a depth of the examination object, insert the at least one virtual scene component into the virtual 3D surface model at a location corresponding to a desired start point for medical imaging the examination object, the virtual scene component being an object or element that is not contained in the real scene and is therefore not imaged via at least one of the depth image sensor and the 2D camera, the processor configured to insert the virtual scene component by (i) creating a geometric description of the at least one virtual scene component, the geometric description including a profile curve representing the depth of the examination object, and (ii) inserting the at least one virtual scene component into the virtual 3D surface model based on the profile curve such that a curvature of the at least one virtual scene component in the virtual 3D surface model corresponds to the depth of the examination object, generate the output image using perspective projection to project the 2D image data corresponding to the second perspective along optical rays of the 2D camera onto the virtual 3D surface model including the at least one virtual scene component such that the output image is a 2D image illustrating a perspectival correct version of the at least one virtual scene component, and set a scan region for the medical imaging of the examination object based on the perspectival correct version of the at least one virtual scene component included in the output image.

15. The device of claim 14, wherein the 2D camera and the depth image sensor are combined to form a camera unit.

16. A medical imaging facility, comprising the device of claim 14.

17. The medical imaging facility of claim 16, wherein the medical imaging facility is a computer tomography apparatus.

18. A medical imaging facility, comprising the device of claim 15.

19. The medical imaging facility of claim 18, wherein the medical imaging facility is a computer tomography apparatus.

* * * * *